(12) United States Patent
Ryan et al.

(10) Patent No.: US 9,113,785 B2
(45) Date of Patent: *Aug. 25, 2015

(54) FLUID MEDIA FOR BIO-SENSITIVE APPLICATIONS

(75) Inventors: S. Eric Ryan, Hopkinton, MA (US); Jing Tang, Arlington, MA (US); Matthew Flinders, Watertown, MA (US)

(73) Assignee: CORNOVA, INC., West Medford, MA (US)

( * ) Notice: Subject to any disclaimer, the term of this patent is extended or adjusted under 35 U.S.C. 154(b) by 1032 days.

This patent is subject to a terminal disclaimer.

(21) Appl. No.: 12/520,022

(22) PCT Filed: Dec. 21, 2007

(86) PCT No.: PCT/US2007/088697
§ 371 (c)(1),
(2), (4) Date: Jun. 18, 2009

(87) PCT Pub. No.: WO2008/080121
PCT Pub. Date: Jul. 3, 2008

(65) Prior Publication Data
US 2010/0049182 A1    Feb. 25, 2010

Related U.S. Application Data

(60) Provisional application No. 60/871,510, filed on Dec. 22, 2006, provisional application No. 60/884,630, filed on Jan. 12, 2007, provisional application No. 60/945,481, filed on Jun. 21, 2007.

(51) Int. Cl.
*A61B 6/00* (2006.01)
*A61B 5/00* (2006.01)
(Continued)

(52) U.S. Cl.
CPC ............ *A61B 5/0075* (2013.01); *A61B 5/0084* (2013.01); *A61B 5/6853* (2013.01);
(Continued)

(58) Field of Classification Search
USPC ........................................ 600/474, 478, 480
See application file for complete search history.

(56) References Cited

U.S. PATENT DOCUMENTS

| | | | |
|---|---|---|---|
| 4,799,479 A * | 1/1989 | Spears | ........................... 606/28 |
| 4,892,099 A | 1/1990 | Ohkawa et al. | |

(Continued)

FOREIGN PATENT DOCUMENTS

WO    2008/080121 A1    7/2008

OTHER PUBLICATIONS

International Search Report dated May 27, 2010 and Written Opinion of the International Searching Authority dated May 27, 2010, each issued in corresponding International Application No. PCT/US2009/060814.

(Continued)

*Primary Examiner* — Long V Le
*Assistant Examiner* — Ellsworth Weatherby
(74) *Attorney, Agent, or Firm* — Onello & Mello, LLP.

(57) ABSTRACT

Systems, methods, and apparatus for providing a fluid and reduced-toxicity optical media with optical analysis and therapeutic energy delivery. An aspect of the invention provides an aqueous solution of increased-salinity of between about 1% and 35%. An increasing salinity in accordance with the invention provides improved transmissive efficiency at many wavelengths and less toxicity than many existing systems and methods. A catheter having integrated fibers for probing or treating internal lumens or other tissues can include a liquid-inflatable balloon or flushing mechanism using the solution for displacing blood or other obstructions in an optical path between the fiber and targeted tissue. Methods including spectroscopy can be employed with the solution for diagnosing medical conditions associated with diseased vessels or other tissues while reducing the risk of permanent damage resulting from the diagnosis. Additional applications include the deliver of therapeutic radiation externally and internally to tissues through h the solution media.

19 Claims, 7 Drawing Sheets

(51) Int. Cl.
*A61B 18/24* (2006.01)
*A61B 17/00* (2006.01)
*A61B 17/22* (2006.01)
*A61B 18/00* (2006.01)

(52) U.S. Cl.
CPC .............. *A61B 18/24* (2013.01); *A61B 5/0066* (2013.01); *A61B 5/0086* (2013.01); *A61B 2017/00274* (2013.01); *A61B 2017/22051* (2013.01); *A61B 2018/00547* (2013.01); *A61B 2562/146* (2013.01)

(56) References Cited

U.S. PATENT DOCUMENTS

| | | | |
|---|---|---|---|
| 5,024,668 A * | 6/1991 | Peters et al. | 606/194 |
| 5,163,950 A | 11/1992 | Pinchuk et al. | |
| 5,496,309 A | 3/1996 | Saadat et al. | |
| 5,496,311 A * | 3/1996 | Abele et al. | 606/28 |
| 5,935,075 A * | 8/1999 | Casscells et al. | 600/474 |
| 5,964,751 A | 10/1999 | Amplatz et al. | |
| 6,148,222 A * | 11/2000 | Ramsey, III | 600/380 |
| 6,529,770 B1 | 3/2003 | Grimblatov | |
| 6,741,884 B1 * | 5/2004 | Freeman et al. | 600/473 |
| 6,847,490 B1 * | 1/2005 | Nordstrom et al. | 359/642 |
| 7,239,782 B1 | 7/2007 | Treado et al. | |
| 7,603,166 B2 * | 10/2009 | Casscells, III et al. | 600/473 |
| 2002/0068853 A1 * | 6/2002 | Adler | 600/160 |
| 2002/0127632 A1 * | 9/2002 | Richards-Kortum et al. | 435/40.51 |
| 2002/0156380 A1 * | 10/2002 | Feld et al. | 600/473 |
| 2002/0183735 A1 | 12/2002 | Edwards et al. | |
| 2003/0073908 A1 * | 4/2003 | Desai | 600/464 |
| 2003/0120207 A1 | 6/2003 | Wang | |
| 2004/0034279 A1 | 2/2004 | Arai et al. | |
| 2004/0077950 A1 * | 4/2004 | Marshik-Geurts et al. | 600/475 |
| 2005/0171527 A1 * | 8/2005 | Bhola | 606/41 |
| 2005/0203434 A1 * | 9/2005 | Kassab | 600/547 |
| 2006/0024007 A1 | 2/2006 | Carlin et al. | |
| 2007/0078500 A1 | 4/2007 | Ryan et al. | |
| 2007/0282301 A1 | 12/2007 | Segalescu et al. | |

OTHER PUBLICATIONS

International Search Report and Written Opinion issued on Apr. 30, 2008 in corresponding International Patent Application No. PCT/US2007/088697.

"Systems and Methods for Analysis and Treatment of a Body Lumen" Specification, Drawings, and Prosecution History, of U.S. Appl. No. 11/537,258, filed Sep. 29, 2006, by S. Eric Ryan, et al., which is stored in the United States Patent and Trademark Office (USPTO) Image File Wrapper (IFW) system.

"Multi-Faceted Optical Reflector" Specification, Drawings, and Prosecution History, of U.S. Appl. No. 11/834,096, filed Aug. 6, 2007, by Jing Tang, et al., which is stored in the United States Patent and Trademark Office (USPTO) Image File Wrapper (IFW) system.

Jean-Joseph Max and Camille Chapados, "Subtraction of the Water Spectra from Infrared Spectra of Acidic and Alkaline Solutions", Applied Spectroscopy, vol. 52, No. 7, pp. 963-969 (Nov. 12, 1997).

Jean-Joseph Max, et al., "Subtraction of the Water Spectra from the Infrared Spectrum of Saline Solutions", Applied Spectroscopy, vol. 52, No. 2, pp. 234-239 (Jul. 11, 1997).

Thomas J. Dougherty and Julia G. Levy, Biomedical Photonics Handbook, ch. 40.17, Tuan Vo-Dinh, Ed., CRC Press, New York (2003).

Ravindra K. Pandey, Biomedical Photonics Handbook, ch. 37, Tuan Vo-Dinh, Ed., CRC Press, New York (2003).

International Search Report and Written Opinion dated Feb. 7, 2011 issued in related International Application No. PCT/US2010/035677.

* cited by examiner

FLUID MEDIA FOR BIO-SENSITIVE APPLICATIONS

RELATED APPLICATIONS

This application claims the benefit of U.S. Patent Application No. 60/871,510 filed Dec. 22, 2006, entitled "Fluid Media for Bio-Sensitive Applications," U.S. Patent Application No. 60/884,630 filed Jan. 12, 2007, entitled "Multi-Faceted Optical Reflector," U.S. Patent Application No. 60/945,481 filed Jun. 21, 2007, entitled "Systems and Methods for Guiding the Analysis and Treatment of a Body Lumen," the entire contents of each of which is herein incorporated by reference.

This application is related to U.S. patent application Ser. No. 11/537,258, filed Sep. 29, 2006 entitled "Systems and Methods for Analysis and Treatment of a Body Lumen," and U.S. patent application Ser. No. 11/834,096 filed Aug. 6, 2007 entitled "Multi-Faceted Optical Reflector," the entire contents of each of which is herein incorporated by reference.

FIELD OF THE INVENTION

This invention generally relates to fluid media for use in transmitting optical radiation, and more particularly to fluid media placed across transmission paths used by optical delivery, treatment, and measurement devices, including intravascular medical devices.

BACKGROUND OF THE INVENTION

Many optical devices rely on the use of and/or interface with forms of fluid media for transmitting radiation. In various applications, certain types of fluid material may provide a necessary medium through which targets are analyzed or treated and for providing safe malleable structural support to a device component. For example, certain types of bio-sensitive material may be damaged or degraded when exposed to air or other environmental factors. When examining or treating bio-sensitive material with light radiation, a relatively safe intervening fluid media is generally preferred. For example, a liquid media such as water might be used to interface with the internal tissue of a patient (e.g., for displacing tissue material, cleaning, and cooling) where that tissue would otherwise be damaged by a direct interface with air The displacement of blood and tissue debris by the introduction of a temporary fluid media is useful, for example, in inspecting narrow passages including blood vessels. Fluid media may be used to provide temporary physical support for holding catheter probes in place during treatment and/or analysis. For example, U.S. Pat. No. 5,964,751, the entire contents of which are incorporated herein by reference, characterizes a catheter having an expandable balloon at its distal end through which the interior surfaces of vessels are treated with radiation. Fluid media relied upon for inflating balloons and providing optical media, in particular, have included gases such as air, $CO_2$, and helium or liquids including water and ordinary saline solution of about 0.85% salinity (or a percentage of grams of dissolved NaCl per milliliter of water). Other systems include a process by which blood and other artifacts are directly flushed out of an area targeted for radiation transmission or collection. Flushing a biologically sensitive area with a fluid media can also be useful for preventing overheating, such as during a tissue ablation procedure with the use of a high-energy laser.

The adopted media through which to examine or treat tissue or other delicate material, however, has suffered from many drawbacks, including safety risks, restrictions in fluid dynamics, and/or significant interference with radiation traveling through the media. For example, the sudden release of air or hydrogen into a patient's bloodstream from a broken balloon or similar device could result in injury and/or death. Furthermore, providing sufficient pressure to properly inflate a catheter balloon (e.g. 8-12 atmospheres in an angioplasty type balloon) with a gas such as air or helium through the narrow passages of a catheter could be difficult and/or prohibitively expensive. Water and ordinary physiological saline solution detrimentally absorb and scatter a significant level and range of optical radiation, including many wavelengths in and outside the visible spectrum, and can thus affect the power profile, footprint, cost, and/or complexity of many systems requiring the use of fluid media through which to transmit or collect radiation. Thus, there is a need for providing transmission media that is both safe for introduction into a patient, is practical, and is of improved transmissive efficiency.

SUMMARY OF THE INVENTION

Aspects of the invention include methods and apparatus for providing a transmissively efficient and relatively less toxic media for use in analyzing and/or treating bio-sensitive targets. In one aspect of the invention, a system is provided for distributing light radiation along one or more paths between one or more light sources and a bio-sensitive target such as, for example, an endovascular region of a living patient targeted for diagnosis and/or treatment. In an embodiment, the light radiation travels, at least in part, through a high-salinity saline solution with a salinity of at least about 1%, providing various levels of transmissive efficiency and safety profiles to the bio-sensitive target.

In an embodiment, the saline solution has a salinity between about 1% and 36%. In an embodiment, the saline solution has a salinity between about 1% and 5%. In an embodiment, the saline solution has a salinity between about 5% and 26%. In an embodiment, the saline solution has a salinity between about 26% and 36%.

An embodiment of the invention includes light radiation of wavelengths between about 200 nm and 5,000 nm (e.g., from ultra-violet radiation through infrared radiation). An embodiment of the invention includes fiber optics for transmitting and/or collecting radiation between the bio-sensitive target and the system such as, for example, through a catheter probe positioned in proximity to the bio-sensitive target. An embodiment of the system is connected to a spectrometer or other analysis device that is arranged to receive radiation emanating from the bio-sensitive target. Such a device can provide information about the bio-sensitive target. An embodiment includes a spectrometer configured to scan wavelengths in the range of between about 250 and 5,000 nanometers and in an embodiment, between about 750 and 2500 nanometers and, in an embodiment, between about 1500 to 1850 nanometers. In an embodiment, the type of spectroscopy used includes at least one of fluorescence, light scatter, optical coherence reflectometry, optical coherence tomography, speckle correlometry, Raman, and diffuse reflectance spectroscopy. Benefits of improved optical transmissivity can include, for example, reduced power requirements, reduced complexity, and a reduced need for a high number of costly optical components (e.g., optical fibers, reflectors, and focusing elements).

An embodiment of the invention includes a controller useful for processing data from, for example, a spectrometer or other analysis device. In an embodiment, the controller is programmed to discriminate between spectra from the saline solution and spectra from the bio-sensitive target. In an embodiment, the controller is programmed to characterize one or more pathophysiologic or morphologic factors of tissue including at least one of collagen content, lipid content, calcium content, inflammation, plaque content or the relative positioning of pathophysiologic conditions within the plaque.

In an aspect of the invention, an apparatus for distributing light radiation to or from a bio-sensitive target is provided that includes at least one waveguide, a container holding saline solution between a transmission end of the at least one waveguide and a bio-sensitive target. The saline solution has a salinity of at least about 1% salinity.

In an embodiment, the at least one waveguide is constructed and arranged for transmitting radiation in the wavelength range of between about 750 nanometers to about 2500 nanometers. In an embodiment, the least one waveguide is constructed and arranged for transmitting radiation in the wavelength range of between about 1500 nanometers to about 1800 nanometers.

In an embodiment, the at least one waveguide includes an optical fiber.

In an aspect of the invention, a method is provided for distributing light radiation to or from a bio-sensitive target that includes the steps of: supplying saline solution of at least about 1% salinity across at least one light transmission path to or from the bio-sensitive target; and the step of at least one of delivering or receiving radiation along the light transmission path.

In an embodiment of the invention, the step of supplying saline solution includes filling an enclosed area with the saline solution. In an embodiment, the enclosed area is located about the distal end of a catheter. In an embodiment, the enclosed area includes an inflatable balloon. In an embodiment, the balloon is a lumen-expanding balloon. In an embodiment, the enclosed area includes a rigid sealed enclosure. In an embodiment, the at least one transmission path passes through the enclosed area. In an embodiment, the enclosed area includes a portion that is translucent to the radiation delivered or received across the transmission path. In an embodiment, at least one or more transmission inputs or outputs of a waveguide is enclosed within the enclosed area.

In an embodiment, the step of at least one of delivering and receiving radiation includes delivering or receiving radiation between a catheter and a blood vessel wall.

In an embodiment of the invention, the bio-sensitive target is directly flushed with the solution about the area through which the light is transmitted. In an embodiment, the flushing displaces at least one of blood or other material that is present across the transmission path.

In an embodiment, the method further includes the step of performing spectroscopic analysis on the target through the delivery and receipt of radiation along the at least one light transmission path.

In an embodiment, the spectroscopic analysis is performed with radiation in the wavelength range of between about 750 nanometers and 2500 nanometers.

In an embodiment, the spectroscopic analysis is performed with radiation in the wavelength range of between about 1550 nanometers and 1850 nanometers.

In an embodiment, the spectroscopic analysis is selected from the group of spectroscopy methods consisting of fluorescence, light scatter, optical coherence reflectometry, optical coherence tomography, speckle correlometry, Raman, and diffuse reflectance spectroscopy.

In an embodiment, the method further includes the step of characterizing one or more pathophysiologic or morphologic factors of tissue within an endovascular region.

In an embodiment, the one or more pathophysiologic or morphologic factors of tissue include characteristics of plaque having at least one of collagen content, lipid content, calcium content, inflammation, or the relative positioning of pathophysiologic conditions within the plaque.

In an embodiment, the step of delivering or receiving radiation includes delivering laser therapy. In an embodiment, the laser therapy comprises ultra violet radiation.

In an embodiment, the toxicity of the solution can be limited to accommodate the risks or frequency of direct contact with a bio-sensitive target or to accommodate the type and sensitivity of tissue targeted. For example, for a routine introduction into an endovascular region, the salinity of the saline solution may be limited to between about 1% and 5% salinity to accommodate a moderate risk of temporary injury. For introduction onto an epidermal area or into a urinary tract, for example, the salinity may be increased to varying degrees up to about 36% salinity. In another example, such as for introduction into a tightly sealed and solid enclosure within a catheter's distal end, the saline solution may be made of a near-saturated solution of up to about 36% salinity. The temperature of the saline solution can be adjusted appropriately for the particular application. For example, the solution can be at around 37° C. in order to maintain consistency with standard blood temperature in humans or of lower temperatures to provide a cooling effect in certain applications (e.g., a laser tissue ablation procedure).

In other embodiments of the invention, therapeutic energy can be transmitted through the saline solution in order to treat the bio-sensitive target. In various embodiments of the invention, treatments include at least one of photodynamic therapy (PDT), interstitial laser photocoagulation (ILP), laser interstitial hyperthennia therapy (ILT), and laser lithotripsy such as for, for example, preparatory treatments prior to insertion of a stent or oher implant. In various embodiments of the invention, ultra-violet (between wavelengths of between about 200 nm to 380 nm), visible radiation (about 380 nm to 750 nm), near infra-red (about 750-5000 nm), and mid-infrared radiation (about 5000 to 30,000 nm) is delivered to tissue of various types.

In another aspect of the invention, $CaCl_2$ solution is used as an optical medium such as, for example, where the risk of intravenous exposure is low. In an embodiment of the invention, $CaCl_2$ solution is used in systems such as those described above for delivery to or collection from, for example, epidermal regions, gastrointestinal regions, biliary regions, or urinary systems (and which are, for example, generally considered less sensitive than blood vessels to toxic media).

BRIEF DESCRIPTION OF THE DRAWINGS

The foregoing and other objects, features, and advantages of the invention will be apparent from the more particular description of preferred embodiments of the invention, as illustrated in the accompanying drawings in which like reference characters refer to thesame parts throughout the different views. The drawings are not necessarily to scale, emphasis instead being placed upon illustrating the principles of the invention.

DETAILED DESCRIPTION

Figure 1A:
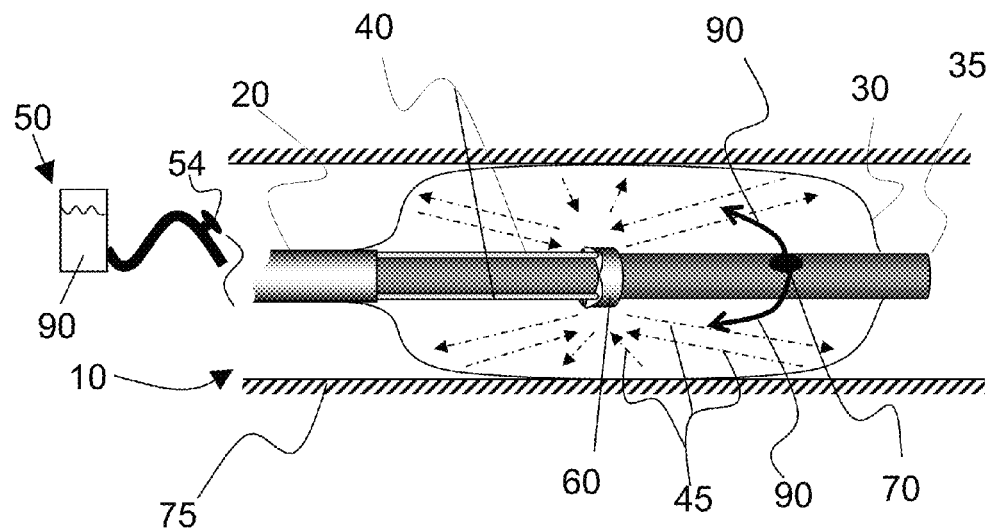
FIG. 1A is an illustrative side perspective view of a balloon catheter probe according to an embodiment of the invention.

Referring to FIG. 1A, an illustrative side perspective view of the distal end of a catheter probe 10 is shown according to an embodiment of the invention. Fibers 40 extend through catheter body 20 along guidewire sheath 35 to a reflecting element 60. A flexible expandable balloon 30 is attached at an end to a protective catheter body 20 and at the opposite end to a guidewire sheath 35, enclosing the ends of fibers 40 and the reflecting element 60. Probe 10 can be inserted into place, for example, within a damaged/diseased vessel wall in accordance with an angioplasty procedure. Fluid media 90 is held in a tank 50 (e.g., as a source of saline solution) from which it is pumped in or removed from balloon 30 by actuation of a knob 54. Fluid media 90 can alternatively be pumped with the use of automated components (e.g.switches/compressors/vacuums). Once in place, balloon 30 can be expanded with fluid media 90 to a pressure of up to, for example, about 8-12 atmospheres in order to prop the balloon surface against vessel walls 75, thereby substantially displacing blood in the luminal region and fixing in place probe 10 with respect to vessel walls 75. Fibers 40 can be connected to a spectrometer, interferometer, or other visualization/analysis device in order to collect, process, and analyze data about vessel walls 75. Radiation distributed to and collected from a lumen wall 75 through balloon 30 is represented by sample trace lines 45. The fluid media 90 comprises an increased-concentration of saline solution over conventional saline solutions. In various embodiments, the concentration of saline solution is between about 1% salinity to about 35% salinity (whereas a normal grade saline solution is of about 0.85% salinity). In an embodiment, the fluid media 90 is output from a port 70.

Figure 3:
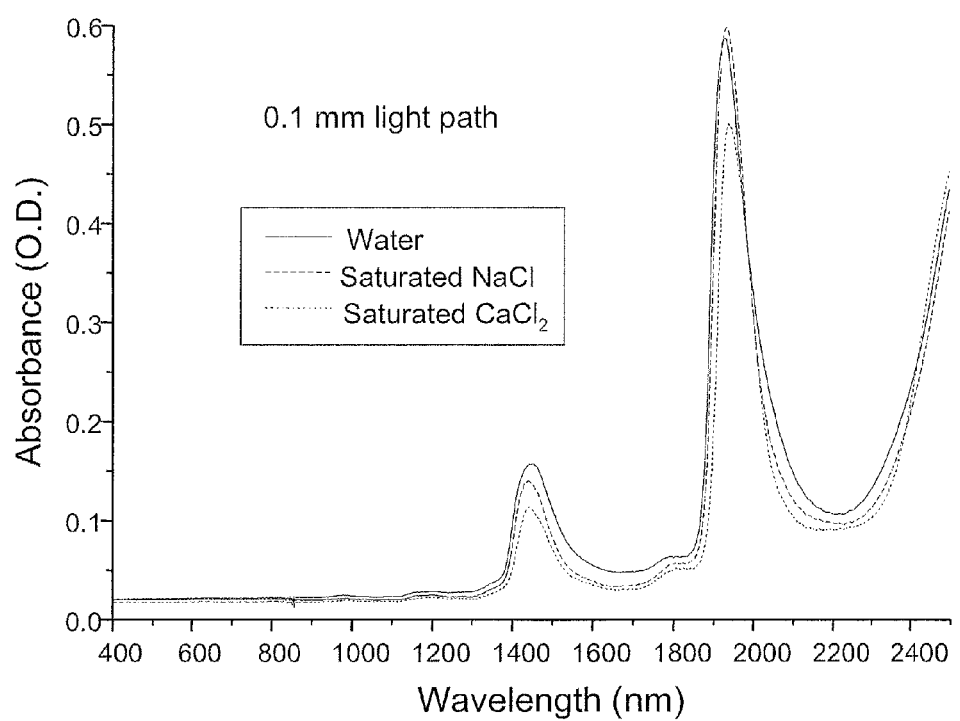
FIG. 3 is a chart of an absorption study comparing radiation traveling through various types of optical transmission media about 0.1 mm in span.

Increasing levels of salinity as compared to standard grade saline solution can significantly improve the light transmission characteristics of the probe 10 while still maintaining acceptable safety profiles. Referring to FIG. 3, a graphical representation of an experiment comparing the relative efficiency of optical transmissions through various types of fluid media is shown. A spectrometer, specifically, a Perkin-Elmer Lambda 9 Spectrometer, measured absorbance through a scan range of approximately 400 nm to 2400 nm across a 0.1 mm thick span over three types of fluid media maintained at room temperature (about 22° C.), including plain water, saturated saline solution (about 35-36% salinity), and saturated calcium chloride ($CaCl_2$) solution (about 74.5% salinity). The experiment exhibited that a medium of increased salinity saline solution and calcium chloride can improve the efficiency of optical transmissions in comparison to a medium of normal water. Increased transmissivity can be observed across the measured spectrum and particularly approaching the near infrared region (or beyond about 750 nanometers).

Figure 4A:
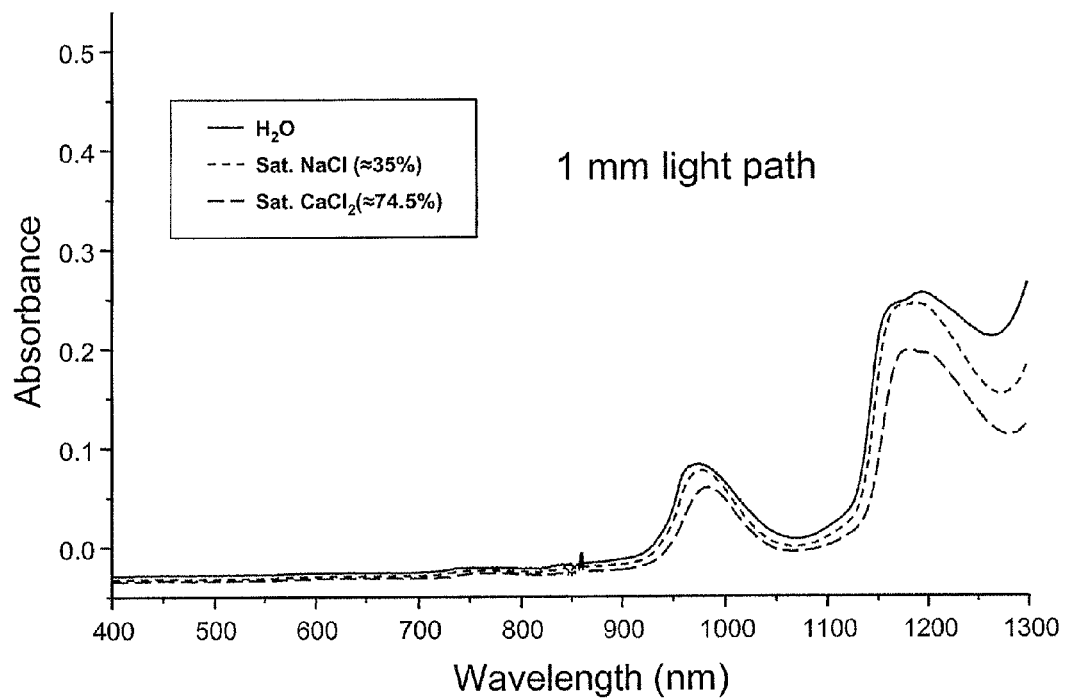
FIG. 4A is a chart of an absorption study comparing radiation traveling through various types of optical transmission media about 1 mm in span.
Figure 4B:
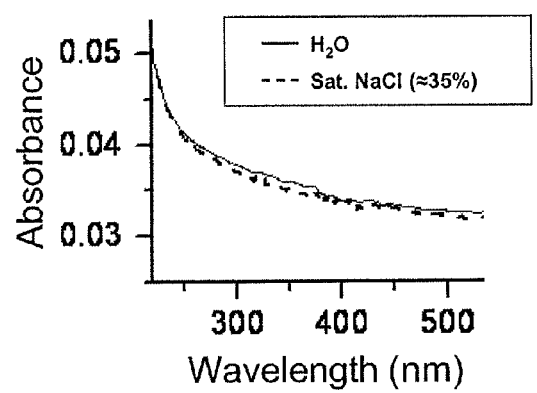
FIG. 4B is a chart of an absorption study comparing radiation inclusive of the ultraviolet region traveling through various types of optical transmission media about 1 mm in span.

Other studies indicate that improved transmissivity extends at least into regions of the infrared spectrum (J-J Max et al., "Subtraction of the Water Spectra from the Infrared Spectra of Acidic and Alkaline Solutions", Applied Spectroscopy, Vol. 52, No. 7, pp. 963-969 (February 1998); J-J Max et al., "Subtraction of the Water Spectra from the Infrared Spectrum of Saline Solutions", Applied Spectroscopy, Vol. 52, No. 2, pp. 234-239 (February 1998)) the entire contents of each of which are incorporated herein by reference, such as, for example, between wavelengths of between about 700 and 5,000 nm. The improved transmissivity of saline solution appears to be generally related to the interaction between the ionic bonding of $Na^+$ and/or $Cl^-$ ions with the water molecules ($H_2O$) that generally results in reduced interaction/absorption of radiation with the solution. Embodiments of the invention may be applied to adaptations of, for example, infrared applications such as the infrared endoscopic balloon probes characterized in, for example, U.S. patent application Ser. No. 11/537,258 (published under Publication No. US20070078500A1), and U.S. Pat. No. 6,741,884 by Freeman et al. (the entire contents of each of which is herein incorporated by reference). Referring to FIGS. 4A-4B, further studies were performed measuring absorbance across a 1 mm span of the same types of media studied in reference to FIG. 3. The Perkin-Elmer spectrometer scanned across a range of wavelengths between about 400 and 1300 nm. The study illustrates that, as the amount of media traveled through increases, the relative difference of absorbance between water and saturated saline solution also increases. Referring to FIG. 4B, additional absorbance measurements were made, including over the ultraviolet span (between about 200 to 380 nm), where small improvements in optical transmissivity are present through an increased salinity (about 35%) solution in comparison to normal water.

Figure 5:
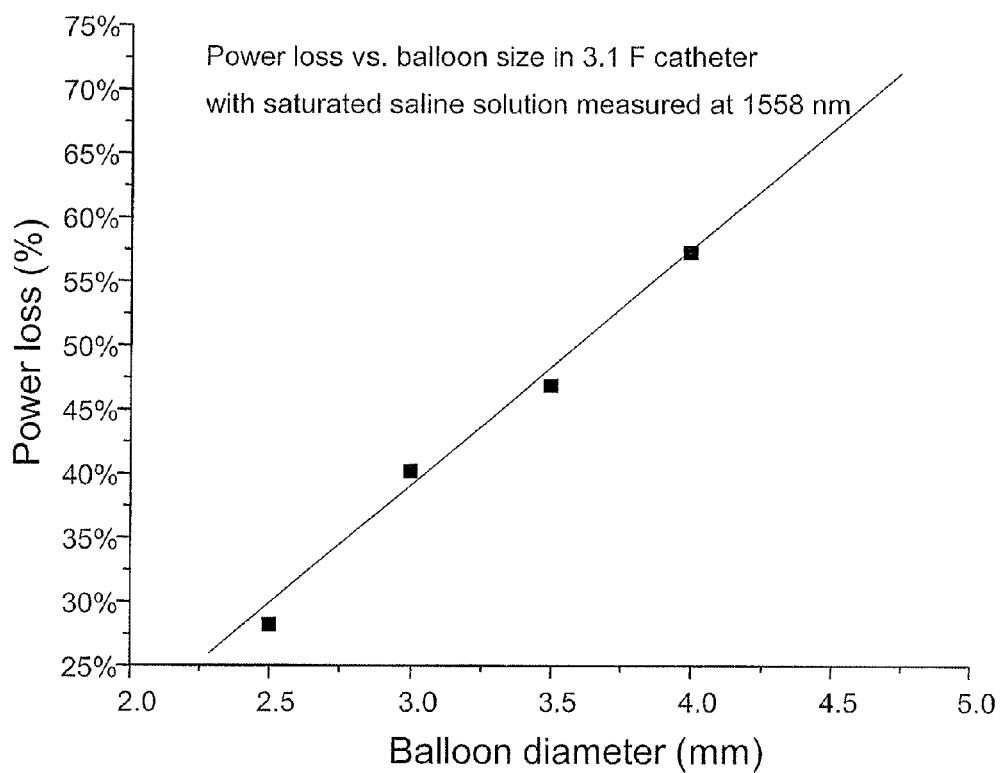
FIG. 5 is a chart of a study comparing the power loss of near-infrared radiation (1558 nm) traveling through a saline-filled balloon with the diameter of the balloon.

Referring to FIG. 5, the power loss of radiation (at a wavelength of 1558 nm) traveling through a balloon catheter of the type described in FIG. 1A was measured in comparison to the diameter of the expanded balloon. The balloon (as in balloon 30 of FIG. 1A) was filled with a saturated saline solution (as through a port 70 in FIG. 1A). Fibers (as in fibers 40 of FIG. 1A) comprised delivery and collection fibers that distributed and collected radiation traveling between the delivery fibers through saturated saline solution (as in solution 90 of FIG. 1A) and a reflective surface on the outside of the balloon. The measurements of power loss indicate that, as the balloon expanded further (and as the span of saline solution along the transmission path increased) there was a proportional loss of power.

While increased salinity solutions can measurably improve the transmissive efficiency in optical catheter probes such as those described herein and in the prior art, higher concentrations of saline solution of greater than about 0.85% salinity may cause damage to a patient if released intravenously. The introduction of calcium chloride can be even more risky, especially in connection with intravenous applications. However, the risk of permanent damage from saline solution can generally be minimized if the concentration and volume of saline solution are limited and measured against, for example, the risk of release, the area of release, and the health of the patient. For example, referring again to FIG. 1A, an embodiment of balloon 30 can be limited to a fluid volume of about 0.164 ml in a coronary catheter (which is typical volume of many expanded angioplasty balloons). The risk of breakage of the balloon 30 can be made small (based on statistics of a similarly designed and medically approved angioplasty-type balloons) and the risk of permanent catastrophic damage from the release of about 35% salinity may also be relatively small. The risk to most patients may still be lower than the risk of using air or many other gases and solutions presently proposed. The risks of a particular salinity and volume of a solution can also be considered in relation to the area of potential release. For example, if the release were to occur in an intravenous area of rapid flow, a rapid dispersal of the solution within the patients would likely occur and, thus, could involve a lower risk of harm.

Figure 1B:
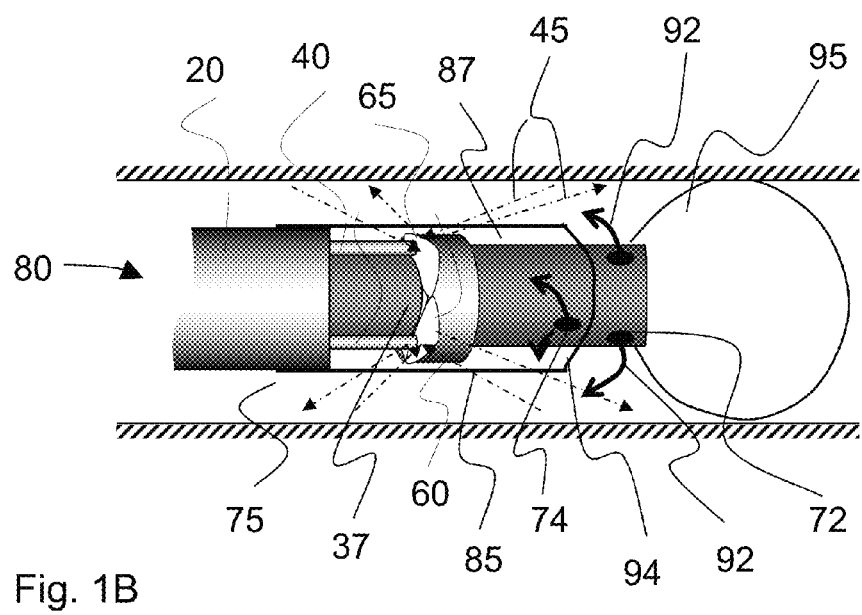
FIG. 1B is an illustrative side-perspective view of a catheter probe according to an embodiment of the invention.
Figure 2A:
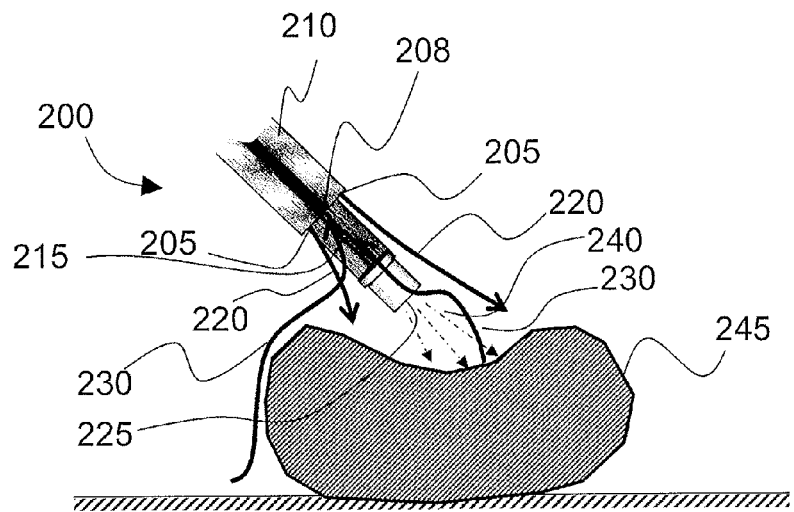
FIG. 2A is an illustrative perspective view of a laser treatment head for external applications according to an embodiment of the invention.
Figure 2B:
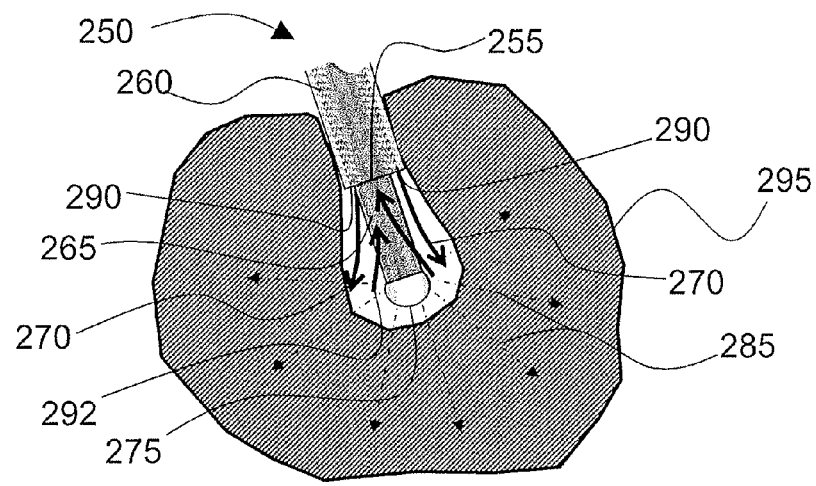
FIG. 2B is an illustrative perspective view of a laser treatment head for internal applications according to an embodiment of the invention.

Certain applications, such as that herein described in reference to FIGS. 1B and 2A-B, may involve the direct flushing of fluid media into an area for the purpose of displacing blood or other body fluids. Referring to FIG. 1B, an illustrative side-perspective view of a catheter probe 80 is shown having a catheter body 37 with a solid transparent covering 85 through which radiation is transmitted and/or collected via integrated fibers 40 and reflective facets 65. An inflatable anchoring balloon 95 is shown inflated for holding catheter probe 80 in place against vessel walls 75. After probe 80 is in place, radiation delivery/collection and visualization/analysis can be implemented while a saline solution 92 is flushed through ports 72 in order to displace blood or other materials along the optical transmission paths between fibers 40 and the vessel walls 75. A saline solution found to be of reasonably low toxicity, such as that of up to about 5% salinity, for example, could be tolerable for direct release into the bloodstream. Certain areas on or within a human patient may be more tolerant to contact with higher salinity solutions or calcium chloride solutions such as, for example, the epidermis, the intestines, or urinary tract.

An added benefit of directly contacting higher salinity or calcium chloride solutions with tissue can be their dehydrating effect. When water or other fluids are drawn out of the targeted tissue by the effect of contact with the solution, interference associated with light transmissions passing through the normally present fluids can be reduced. With less interference, improved efficiency and deeper penetration across various wavelengths can be achieved. Diffuse reflectance spectroscopy, for example, can be enhanced where radiation travels deeper into the tissue. Laser therapy can also work more effectively and faster with reduced interference.

Figure 6:
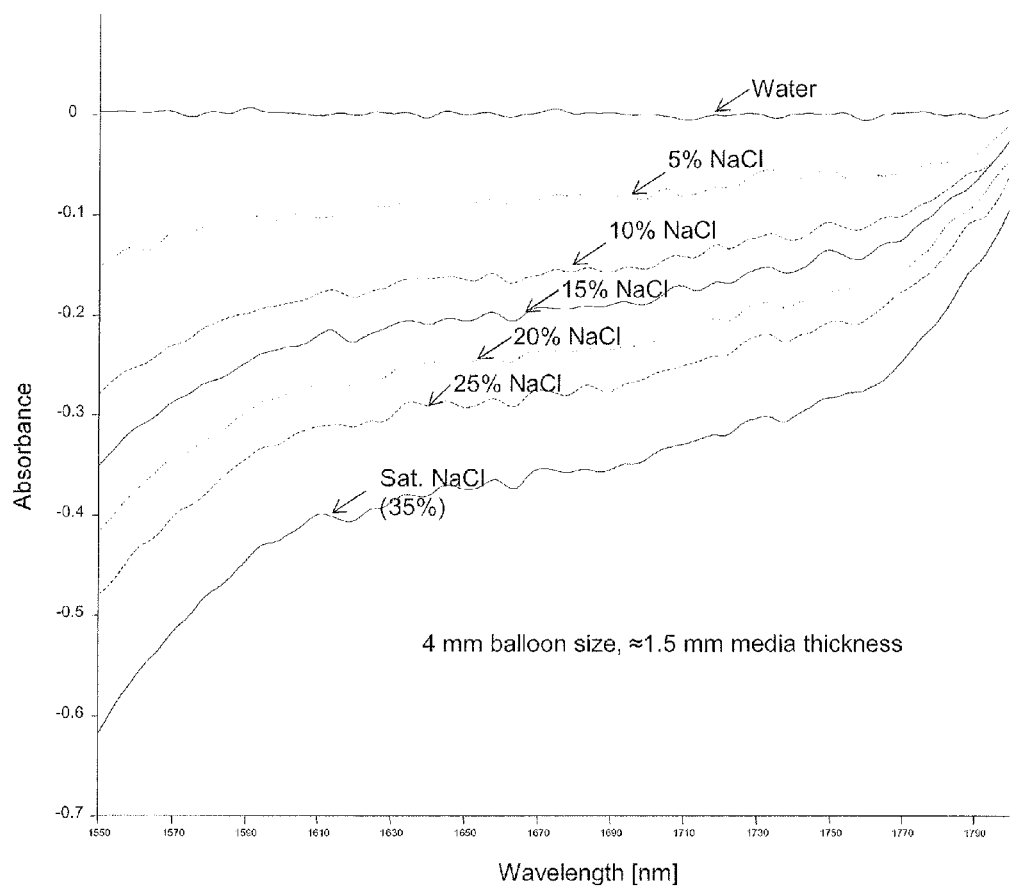
FIG. 6 is a chart of an absorption study of radiation traveling through various concentrations of saline solution.

Referring to FIG. 6, a further study was performed by comparing the transmissive efficiency of radiation traveling through media having varying levels of salinity. The study was performed using an Axsun Technologies IntegraSpec XL CH spectrometer across a wavelength range (1550 to 1790 nm) within the near infrared region. Scans over the wavelength range were performed separately across about 1.5 mm spans of increasing salinity solutions (i.e., normal water, 5% salinity, 10% salinity, 15% salinity, 15% salinity, 20% salinity, 25% salinity, and 35% salinity) at about room temperature (about 22° C.). The scans demonstrate that intermediate levels of salinity (between zero and saturation) can provide benefits in transmissive efficiency over water and standard grade saline solutions (0.85% salinity). Thus, the salinity of solutions used in such applications as discussed herein may be moderated based on safety risks while still providing benefits over previously adopted fluid media with similar applications.

Referring again to FIG. 1B, the intervening area 87 between covering 85 and catheter body 37 is also preferably filled through port 74 with a relatively non-toxic and transmissively efficient media 94 such as those described above in accordance with other embodiments of the invention. The solid and transparent covering 85 can provide a lower risk of breakage and can reduce the risk of accidental introduction of media into the bloodstream. Thus, even higher concentrations of saline may be tolerable within the solid structure of the probe as compared to, for example, inflatable balloons and can provide even greater transmissive efficiency. Saturated saline solutions of salinity up to about 35%, for example, can be used.

The operational temperature of the saline solution can be, for example, about typical human blood temperature (37° C.) for improved biological compatibility. The solution may also be of lower temperatures in order to provide a cooling effect such as in a laser tissue ablation procedure. While pressure and temperature can significantly affect the solubility of certain solutions, the solubility (saturation point) of sodium chloride in water is known to be highly stable and remains at about 35%, including at temperatures approaching freezing, with moderate increases as temperatures go beyond room temperature and as pressures are increased beyond normal atmospheric pressure. Maintaining sodium chloride in solution at about 35% salinity or less during transport, storage, and use is thus highly feasible.

Analysis through probes such as, for example, shown in FIGS. 1A-1B can include various types of spectroscopy and/or interferometry, including fluorescence, light scatter, optical coherence reflectometry, optical coherence tomography, speckle correlometry, Raman, and diffuse reflectance spectroscopy. Spectra may be taken over the visible and/or non-visible spectrums including from between, for example, between about 250 and 2500 nanometers, and further in between about 750 and 2500 nanometers (near infrared) and over single or multiple wavelength bands therein. Diffuse reflectance spectroscopy in the near infrared region, for example, is known to provide information about pathophysiologic and morphologic factors of tissue. A controller (not shown for clarity) can be connected with the catheter system and programmed to obtain various information from spectroscopic readings such as, for example, pathophysiologic or morphologic factors of tissue such as plaque content and shape along with collagen content, lipid content, calcium content, inflammation, or the relative positioning of pathophysiologic conditions within the plaque. The controller is preferably configured to particularly discriminate between the spectra of the employed media (i.e. a specific % salinity solution) and the spectra of targeted tissue or other material being analyzed. A number of techniques are available for discriminating between saline spectra and other spectra (e.g., see J-J Max et al., "Subtraction of the Water Spectra from the Infrared Spectrum of Saline Solutions", Applied Spectroscopy, Vol. 52, No. 2, pp. 234-239 (February 1998)), the entire contents of which are incorporated herein by reference. Other examples of catheter probes making use of introducing a fluid media through which optical analysis is performed are described in U.S. Patent Publication No. US 2006/0024007 A1 by Carlin, et al., the contents of which are herein incorporated by reference. Carlin, et al. describe the application of low-coherence interferometry and optical coherence tomography, among other methods, for providing information about lipid pools and other characteristics of vessel walls through an expandable balloon integrated with a catheter probe.

Other embodiments in accordance with the invention can include the use of therapeutic radiation passed through fluid optical media. For instance, the fiber integrated systems of 1A-B can be adapted to deliver therapeutic laser energy, for example, to tissue about the catheter. In further embodiments of the invention, the systems could also deliver radiation to photo-activated drugs embedded on the surface of balloon 30, enclosure 85, or a stent (not shown) placed about balloon 30, and/or to drugs systemically administered in a patient.

Figure 1C:
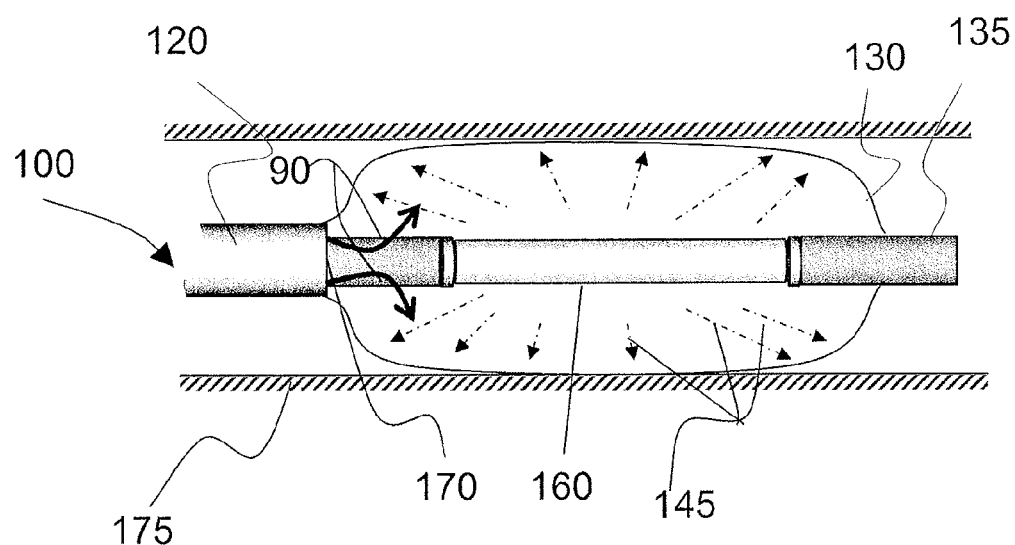
FIG. 1C is an illustrative side-perspective view of a balloon catheter for delivering therapeutic radiation to an intravascular region according to an embodiment of the invention.

Referring to FIG. 1C, a probe end 100 is shown in an embodiment of the invention for use in a light-therapy application. A light-diffusing segment 160 is integrated with a conduit 135 extending from a catheter sheath 120. An inflatable expandable balloon 130 encloses the light-diffusing segment 160 and can be filled with, for example, an increased salinity saline solution 90 by being pumped through catheter sheath 120 and out a port 170. Sample light paths 145 are shown emanating toward the surface of balloon 130 and surrounding surface 175. Light delivered through light-diffusing segment 160 can be of a wavelength and power to provide treatments of various types, including modification and/or destruction of the targeted tissues. For example, photodynamic therapy (PDT) provides treatment for various tissue types having cancerous, pre-cancerous, and degenerative conditions. Wavelengths known to provide biological effects for various tissue types include visible and infrared radiation (e.g., 600 to 800 nm) in addition to shorter wavelengths (Thomas J. Dougherty and Julia G. Levy, in *Biomedical Photonics Handbook*, Tuan Vo-Dinh, Ed., CRC Press, New York (2003), ch. 38)). Additional embodiments of the present invention can be applied to systems described in, for example, U.S. Pat. No. 5,964,751 by Amplatz, et al., the entire contents of which are incorporated herein by reference which describes the use of radiation delivered through clear fluid media to irradiate endothelial and intimal tissue through an angioplasty-like apparatus with "blood flushing capability."

Referring to FIG. 2A, a head 200 of a laser tissue ablation system is shown in an embodiment of the invention. A sheath 210 includes an inner conduit 215 with a laser delivery system (e.g. including a laser fiber assembly) which can provide a precision point source of radiation from tip 225 to epidermal area 245. The type of laser system provided can include, for example, a $CO_2$ laser (e.g. 10,600 nm) or Er:YAG laser (e.g. 2940 nm) which can provide, for example, laser skin resurfacing (LSR) treatment (see supra *Biomedical Photonics Handbook*, ch. 40.17), the entire contents of which are incorporated herein by reference. Before and during treatment, the system can deliver a high-salinity solution 220 through a port 205 to cool epidermal area 245 and/or flush debris. Solution 220 could alternatively be a calcium chloride solution, potentially providing further transmissive efficiency, where the risk of intravenous introduction is limited. Laser radiation 230, 240 can be delivered more efficiently through solution 220 than through a typical physiological saline solution or water. A higher-salinity solution in accordance with the invention may also better draw out potentially interfering fluids (i.e. water) from the epidermal area than would traditional cooling/flushing solutions. A port 208 simultaneously removes used solution 230 and debris through a port 208 via a suction mechanism (not shown). One or more ports (205 and/or 208) can alternatively cycle between both flushing and removal.

Referring to FIG. 2B, a head 250 of an insertable laser delivery system is shown in an embodiment of the invention for treating an internal tissue area 295. A sheath 260 includes an inner conduit 265 having a diffusing tip 275 for delivering thermal radiation 285 (e.g. high energy laser radiation) to internal tissue area 295. The internal tissue can be, for example, cancerous. Laser treatment can be delivered in accordance with, for example, interstitial laser thermotherapy (ILT) (see supra *Biomedical Photonics Handbook*, ch. 42.12), the entire contents of which are incorporated herein by reference, or interstitial laser photocoagulation (ILP) (see supra *Biomedical Photonics Handbook*, ch. 47.2.2.2), the entire contents of which are incorporated herein by reference, with the use of a Nd:YAG laser to generate thermal energy with, for example, infrared and near infrared radiation. A port 290 delivers a higher-salinity saline solution 270 to tissue area 295 in accordance with previous embodiments, and removes used solution 292 through a port 255 via a suction mechanism (not shown). One or more ports (290 and/or 255) can alternatively cycle between both flushing and removal. For positioning head 250 into position, the sheath 260 can have a retractable needle assembly (not shown) for guiding head 250 into tissue area 295 prior to the needle's retraction and subsequent treatment.

Embodiments of the invention can be adapted to include urological and gastrointestinal treatments including laser lithiasis (see supra Biomedical Photonics Handbook, ch. 45.2.1), laser-induced prostatectomy (see supra Biomedical Photonics Handbook, ch. 45.2.2), and photocoagulation of hemorrhaging ulcers (see supra Biomedical Photonics Handbook, ch 46.3), the entire contents of each of which are incorporated herein by reference among others. In embodiments of the invention, a calcium chloride solution can be an appropriate solution in these and other applications where the risk of intravenous exposure is minimized.

It will be understood by those with knowledge in related fields that uses of alternate or varied forms or materials and modifications to the methods disclosed are apparent. This disclosure is intended to cover these and other variations, uses, or other departures from the specific embodiments as come within the art to which the invention pertains.

We claim:

1. A system for probing or treating a bio-sensitive region, said system comprising:
    at least one radiation source and at least one radiation detector;
    a fluid-delivery system comprising a source of saline solution, the saline solution having a salinity of at least 5% to a saturated level of salinity; and
    a controller having a non-transitory computer readable medium programmed with instructions to direct the at least one radiation source to transmit light radiation along one or more light transmission paths between the at least one radiation source, the at least one radiation detector, and the bio-sensitive region while directing the fluid-delivery system to distribute the saline solution across at least a portion of the one or more light transmission paths.

2. The system of claim 1 wherein the one or more light transmission paths comprise one or more waveguides.

3. The system of claim 1 wherein the bio-sensitive region is an endovascular region.

4. The system of claim 1 wherein said saline solution has a salinity of between 5% and 26%.

5. The system of claim 2 further comprising a spectrometer connected to the one or more waveguides and configured and arranged to receive radiation emanating through said saline solution.

6. The system of claim 5 wherein the spectrometer is constructed and arranged to scan one or more wavelengths between about 250 and 2500 nanometers.

7. The system of claim 6 wherein the spectrometer is constructed and arranged to scan one or more wavelengths between about 750 and 2500 nanometers.

8. The system of claim 7 wherein said spectrometer is constructed and arranged to scan one or more wavelengths between about 1500 and 1850 nanometers.

9. The system of claim 5 wherein the spectrometer is configured to perform spectroscopy selected from the group of spectroscopy methods consisting of fluorescence, light scatter, optical coherence reflectometry, optical coherence tomography, speckle correlometry, Raman, and diffuse reflectance spectroscopy.

10. The system of claim 9 further comprising a controller programmed to use said spectroscopy to characterize one or more pathophysiologic or morphologic factors of tissue within an endovascular region.

11. The system of claim 1 wherein said at least a portion of one or more light transmission paths comprises an inflatable balloon disposed about a catheter body.

12. The system of claim 11 wherein said one or more light transmission paths comprise one or more waveguides having at least one of a delivery output and a collection input located within the inflatable balloon.

13. The system of claim 11 further comprising a controller programmed to monitor the level of expansion of said inflatable balloon.

14. An apparatus for distributing light radiation to or from a bio-sensitive region, said apparatus comprising:
   at least one waveguide;
   a container for holding saline solution between a transmission end of said at least one waveguide and a bio-sensitive target; and
   a source of saline solution having a salinity of between 5% and 36%, the source arranged for providing the saline solution to the container; and
   a controller having a non-transitory computer readable medium programmed with instructions to direct at least one radiation source to transmit light radiation through the at least one waveguide while providing the saline solution between a transmission end of the at least one waveguide and the container.

15. The apparatus of claim 14 wherein said at least one waveguide is constructed and arranged for transmitting radiation in the wavelength range of between about 750 nanometers to about 2500 nanometers.

16. The apparatus of claim 15 wherein said at least one waveguide is constructed and arranged for transmitting radiation in the wavelength range of between about 1500 nanometers to about 1850 nanometers.

17. The apparatus of claim 16 wherein said container is a lumen expanding balloon.

18. A system for probing and treating a body lumen comprising:
   a flexible conduit that is elongated along a longitudinal axis suitable for insertion into a body lumen, the conduit having a proximal end and a distal end;
   at least one delivery waveguide and at least one collection waveguide integrated with the flexible conduit;
   at least one radiation source connected to a transmission input of the at least one delivery waveguide, the radiation source constructed and arranged to provide radiation at a wavelength in a range of about 250 to 2500 nanometers;
   at least one optical detector connected to a transmission output of the at least one collection waveguide wherein the transmission output of the at least one collection waveguide is connected to a spectrometer;
   a lumen-expanding inflatable balloon disposed about a portion of the conduit, a transmission output of the at least one delivery waveguide and a transmission input of the at least one collection waveguide located within the balloon; and
   a source of saline solution for filling said lumen-expanding inflatable balloon, wherein said saline solution has a salinity of at least 5% to a salinity of 36%.

19. A method for probing or treating a bio-sensitive region comprising the steps of:
   providing a controller having a non-transitory computer readable medium programmed with instructions to direct at least one radiation source to transmit light radiation along one or more light transmission paths between at least one radiation source, at least one radiation detector, and a bio-sensitive region while directing a fluid-delivery system to distribute a saline solution across at least a portion of the one or more light transmission paths; and
   delivering the saline solution across the at least one light transmission path between the bio-sensitive region, the radiation source, and the radiation detector, while delivering and collecting radiation along the at least one light transmission path, the saline solution having a salinity of between 5% and 36%.

* * * * *